United States Patent [19]

Cox et al.

[11] Patent Number: 5,046,111
[45] Date of Patent: Sep. 3, 1991

[54] METHODS AND APPARATUS FOR OPTICALLY DETERMINING THE ACCEPTABILITY OF PRODUCTS

[75] Inventors: Kenneth A. Cox, Richmond; Robert J. Maher, Midlothian, both of

[73] Assignee: Philip Morris Incorporated, New York, N.Y.

[21] Appl. No.: 308,739

[22] Filed: Feb. 9, 1989

[51] Int. Cl.⁵ .............................................. G06K 9/00
[52] U.S. Cl. ......................................... 382/8; 382/15; 364/552
[58] Field of Search .................... 382/8, 39, 14, 15; 364/552

[56] References Cited

U.S. PATENT DOCUMENTS

| | | | |
|---|---|---|---|
| 4,053,056 | 10/1977 | Day | 209/73 |
| 4,097,845 | 6/1978 | Bacus | 382/6 |
| 4,481,664 | 11/1984 | Linger et al. | 382/8 |
| 4,482,971 | 11/1984 | Blazek | 364/552 |
| 4,637,054 | 1/1987 | Hashim | 382/8 |
| 4,759,074 | 7/1988 | Iadipaolo et al. | 382/23 |
| 4,872,024 | 10/1989 | Nagai et al. | 382/8 |
| 4,926,491 | 5/1990 | Maeda et al. | 382/36 |

FOREIGN PATENT DOCUMENTS 0155789 9/1985 European Pat. Off. .
63-257083 10/1988 Japan .
WO89/10596 11/1989 World Int. Prop. O. .

OTHER PUBLICATIONS

R. C. Gonzalez, *Digital Image Processing*, Addison-Wesley Publishing Company, 1987, pp. 331–341.
W. K. Pratt, *Digital Image Processing*, John Wiley & Sons, Inc., 1978, pp. 478–492.
G. H. Golub et al., "Generalized Cross-Validaiton as a Method for Choosing a Good Ridge Parameter," *Technometrics*, vol. 21, No. 2, May 1979.

*Primary Examiner*—Leo H. Boudreau
*Assistant Examiner*—Steven P. Fallon
*Attorney, Agent, or Firm*—Robert R. Jackson

[57] ABSTRACT

The appearance of a product is determined to be acceptable or unacceptable by computing a discriminant function or image from a plurality of two-dimensional images of products of the kind to be inspected. A two-dimensional image of the product is then formed and processed using the discriminant image to produce an output value which can be compared to a predetermined value used in computing the discriminant image. If the output value deviates from the predetermined value by more than a predetermined amount, the product has been found to have an unacceptable appearance.

34 Claims, 12 Drawing Sheets

FROM FIG. 2b

136 — COMPUTE DISCRIMINANT IMAGE $F_{xy}$.

$$F_{xy} = \sum_{i=1}^{n} (I_{xy}^i) \sum_{j=1}^{s} \frac{B_{iji} \sum_{i'=1}^{n} a_{i'} B_{i'j}}{\gamma_j}$$

140 — ACQUIRE AND PROCESS SAMPLE IMAGE SET.

144 — PERFORM DOT PRODUCT FOR EACH SAMPLE IMAGE.

$$C = \sum_{xy} F_{xy} I_{xy}$$

TO FIG. 2c

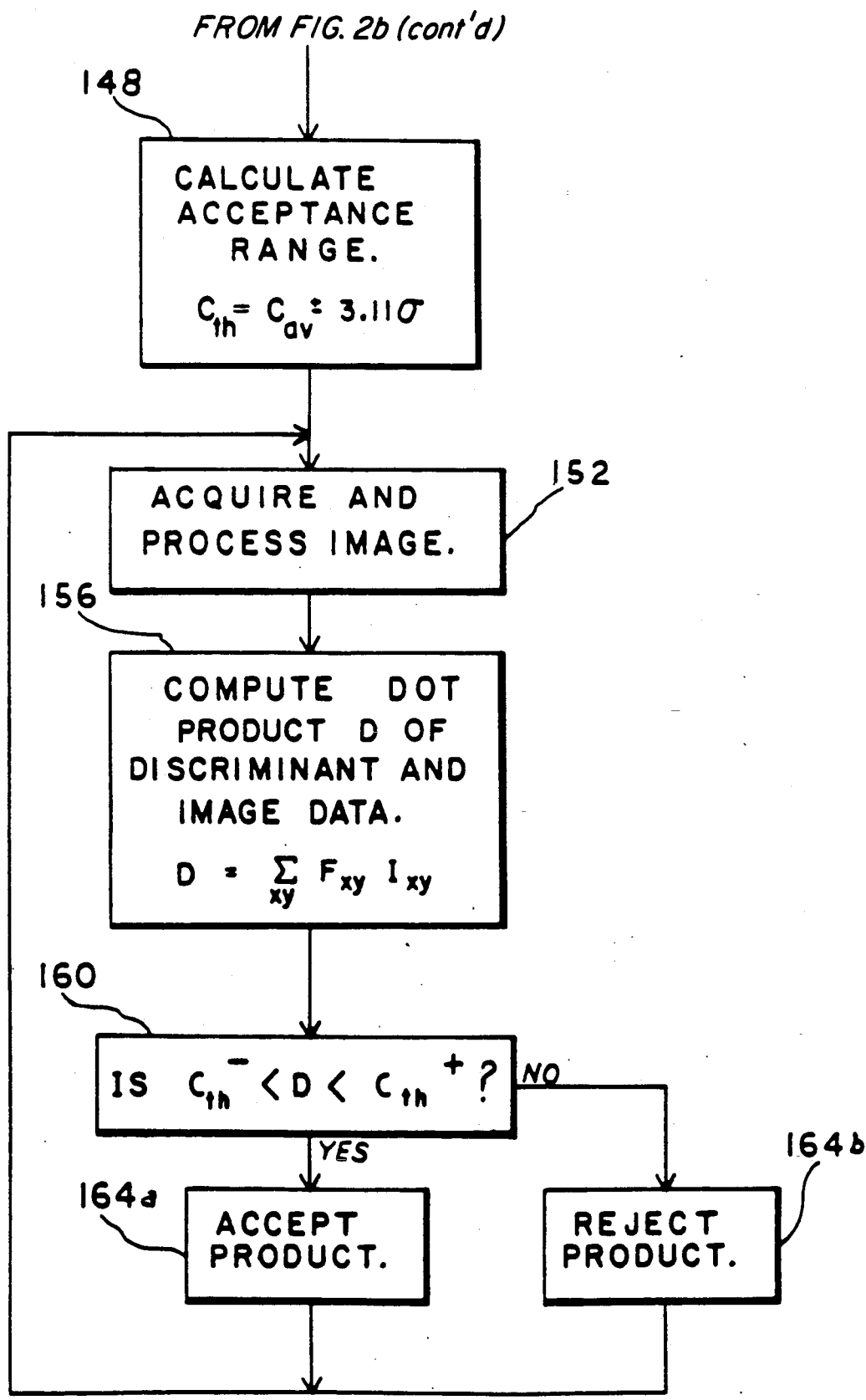

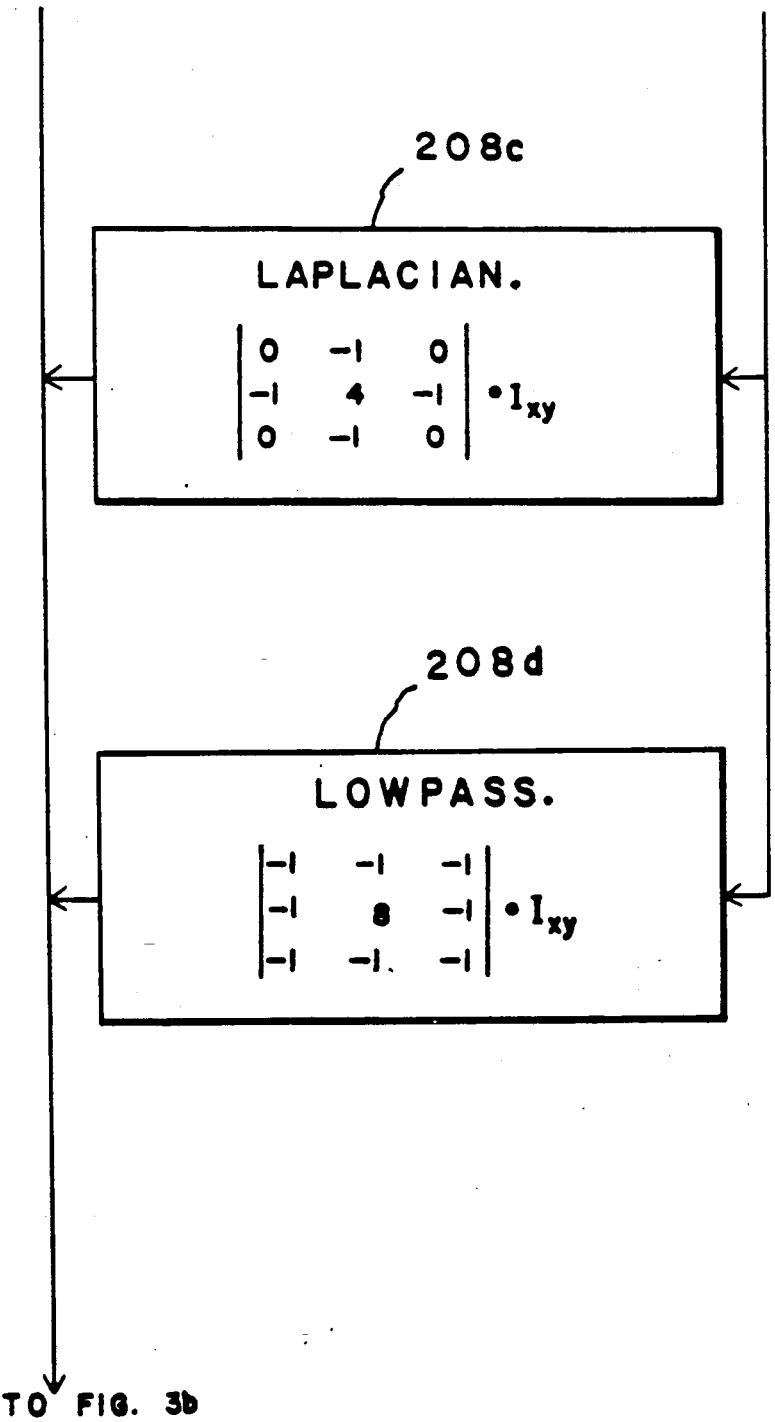

METHODS AND APPARATUS FOR OPTICALLY DETERMINING THE ACCEPTABILITY OF PRODUCTS

BACKGROUND OF THE INVENTION

This invention relates to product inspection methods and apparatus, and more particularly to methods and apparatus for optically determining whether or not a product has an acceptable appearance.

For many products such as consumer goods like packaged foods, beverages, cleaning products, health and beauty aids, cigarettes, cigars, etc., it is very important that the external appearance of the product or its packaging be uniform and defect-free. Yet these products are typically produced in such large quantities and at such high speeds that some form of automated optical inspection is practically essential. Many prior art optical inspection techniques rely on examining only preselected parts of the object being inspected. It is therefore possible for such prior art systems to miss defects occurring in regions other than those preselected for examination, and/or to miss defects of a kind that were not anticipated when the system was set up. Such prior art systems must also be customized for each product inspection task. This requires a high level of skill and is very time-consuming.

In view of the foregoing, it is an object of this invention to provide optical product inspection methods and apparatus which process an overall image of the product being inspected so that a significant defect or deviation from the norm occurring anywhere in the image will cause the associated product to be identified as deviant or defective.

It is another object of this invention to provide optical product inspection methods and apparatus which are of universal application and which can automatically adapt to each new inspection task without requiring elaborate set-up by a highly skilled operator.

It is still another object of this invention to provide optical product inspection methods and apparatus which can automatically acquire the information required to perform each new inspection task without the intervention of a highly skilled operator.

SUMMARY OF THE INVENTION

These and other objects of the invention are accomplished in accordance with the principles of the invention by providing methods and apparatus which compute a filter function or discriminant image from two-dimensional images of a plurality of objects of the kind to be inspected. The discriminant image computation preferably includes a procedure for automatically determining the optimum amount of information from the two-dimensional images to be employed in computing the discriminant image to avoid the introduction of "noise" into the discriminant image which would diminish its effectiveness. After the discriminant image has been computed, a two-dimensional image of each product is formed and processed using the discriminant image to produce an output value which can be compared to a predetermined value used in computing the discriminant image. The appearance of the product is determined to be normal or acceptable if the output value does not deviate from the predetermined value by more than a predetermined amount. Otherwise, the appearance of the product is determined to be non-normal or unacceptable.

Further features of the invention, its nature and various advantages will be more apparent from the accompanying drawings and the following detailed description of the preferred embodiments.

BRIEF DESCRIPTION OF THE DRAWINGS

FIGS. 2a, 2b, and 2c (referred to collectively as FIG. 2) are a flow chart of the optical product inspection method of this invention.

DETAILED DESCRIPTION OF THE PREFERRED EMBODIMENTS

Figure 1:
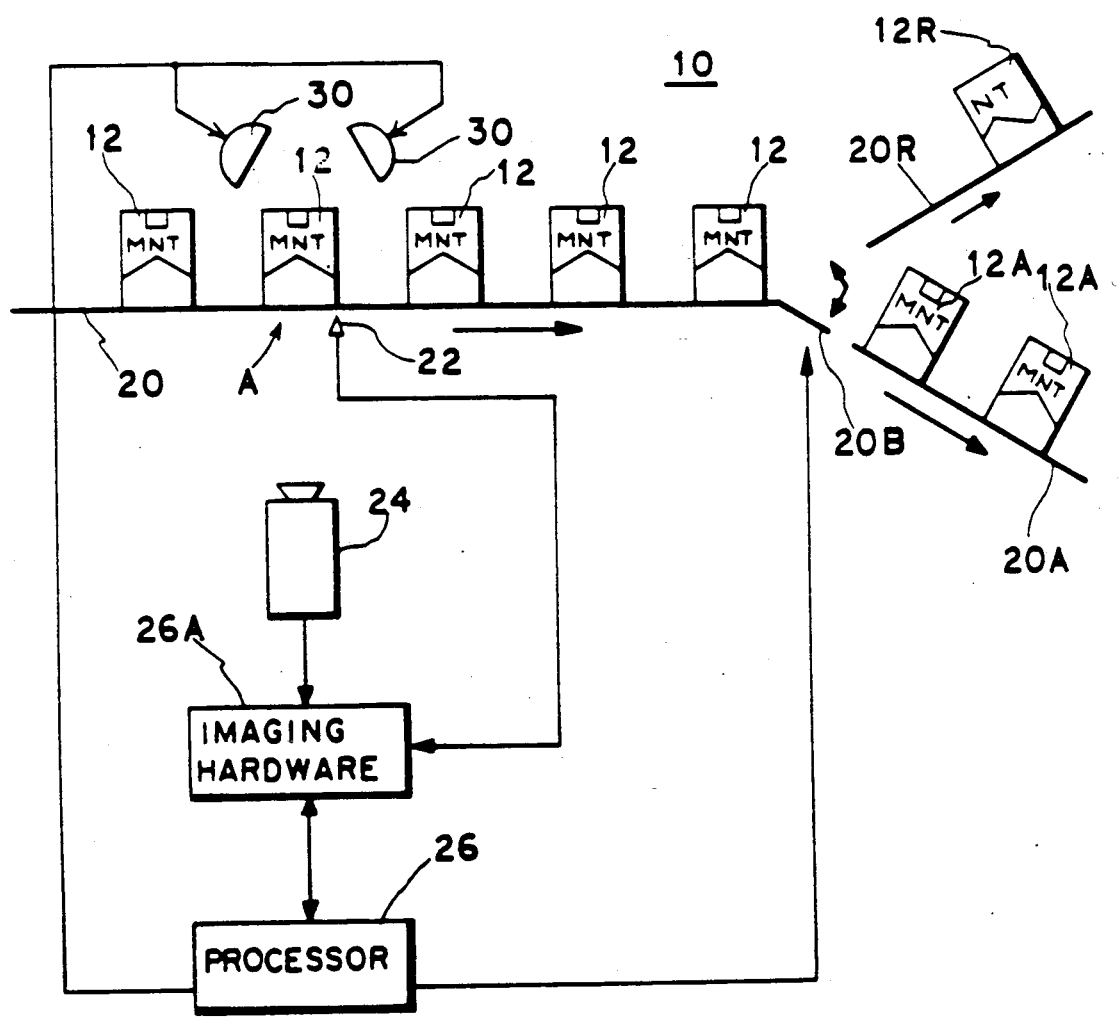
FIG. 1 is a simplified schematic block diagram of an optical product inspection apparatus constructed in accordance with the principles of this invention.

As shown in FIG. 1, typical product inspection apparatus 10 constructed in accordance with this invention includes conveyor apparatus 20 for conveying the objects or products 12 to be inspected, one after another, from left to right as viewed in the FIG. At location A (which is in the field of view of conventional video camera 24) a product 12 is illuminated by light from conventional light sources 30. Each time conventional product sensor 22 detects a product 12 opposite camera 24, imaging hardware 26A (which may be part of processor 26) "grabs" or acquires a two-dimensional image of the product from camera 24. Camera 24 may be a conventional monochrome (e.g., black and white) or polychrome (i.e., color) video camera such as any NTSC or RGB compatible camera. Although it will be apparent to those skilled in the art how the invention can be extended to full color product inspection, for simplicity and clarity only monochrome (e.g., black and white) inspection will be described in detail herein.

Each two-dimensional image acquired by imaging hardware 26A is processed by elements 26 and 26A as described in detail below so that by the time the associated product 12 reaches the controllable branch 20B in conveyor 20, processor 26 has determined whether or not that product has an acceptable image. If the product has an acceptable image, processor 26 controls branch 20B so that the product is directed to conveyor segment 20A which conveys accepted products 12A away for further normal processing. On the other hand, if the product's image is not acceptable, processor 26 controls branch 20B so that the product is directed to conveyor segment 20R which conveys defective and therefore rejected products 12R away for further special handling. Processor 26 is typically a suitably programmed conventional micro- or mini-computer such as a Sun 3/160 workstation available from Sun Microsystems, Inc. of Mountain View, Calif. with a conventional ICS-400 imaging hardware system 26A available from Androx Corporation of Canton, Mass.

Figure 2A:
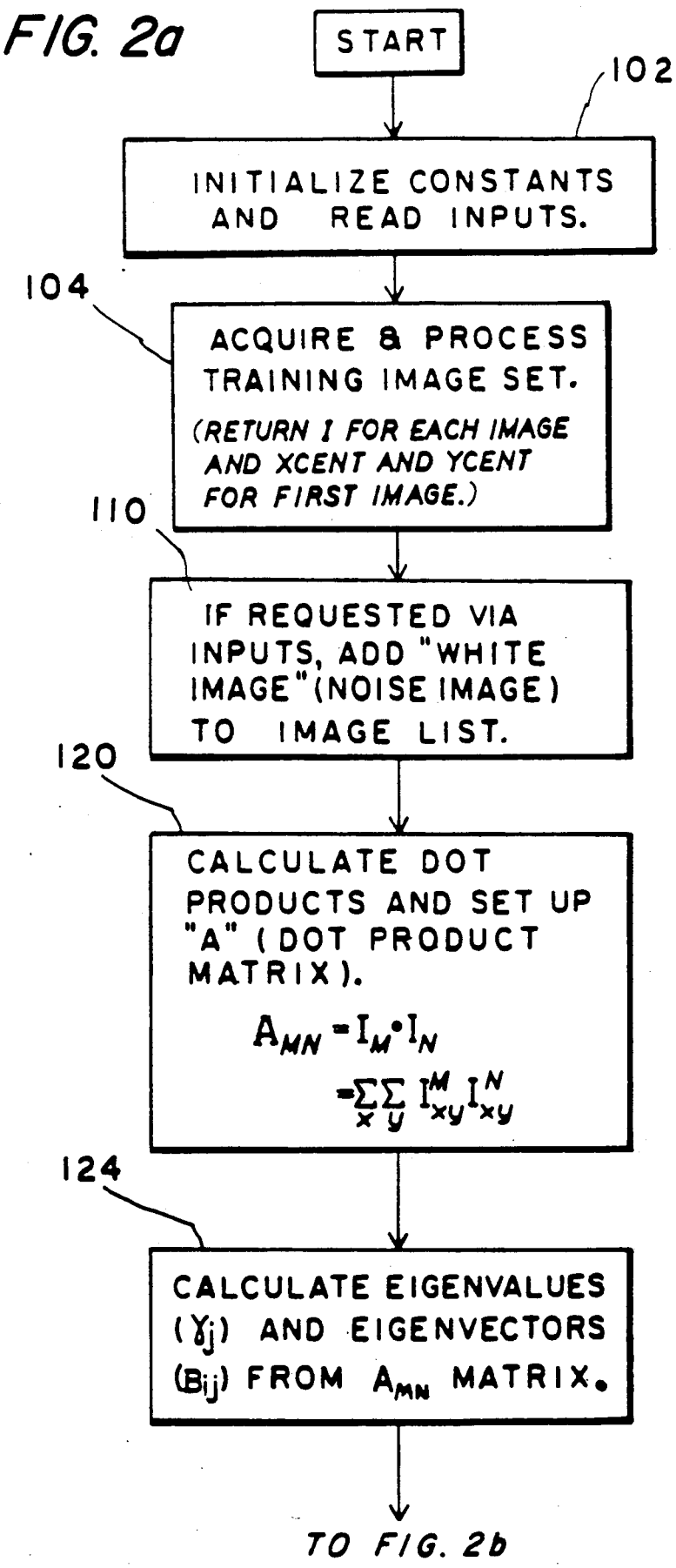
Figure 2B:
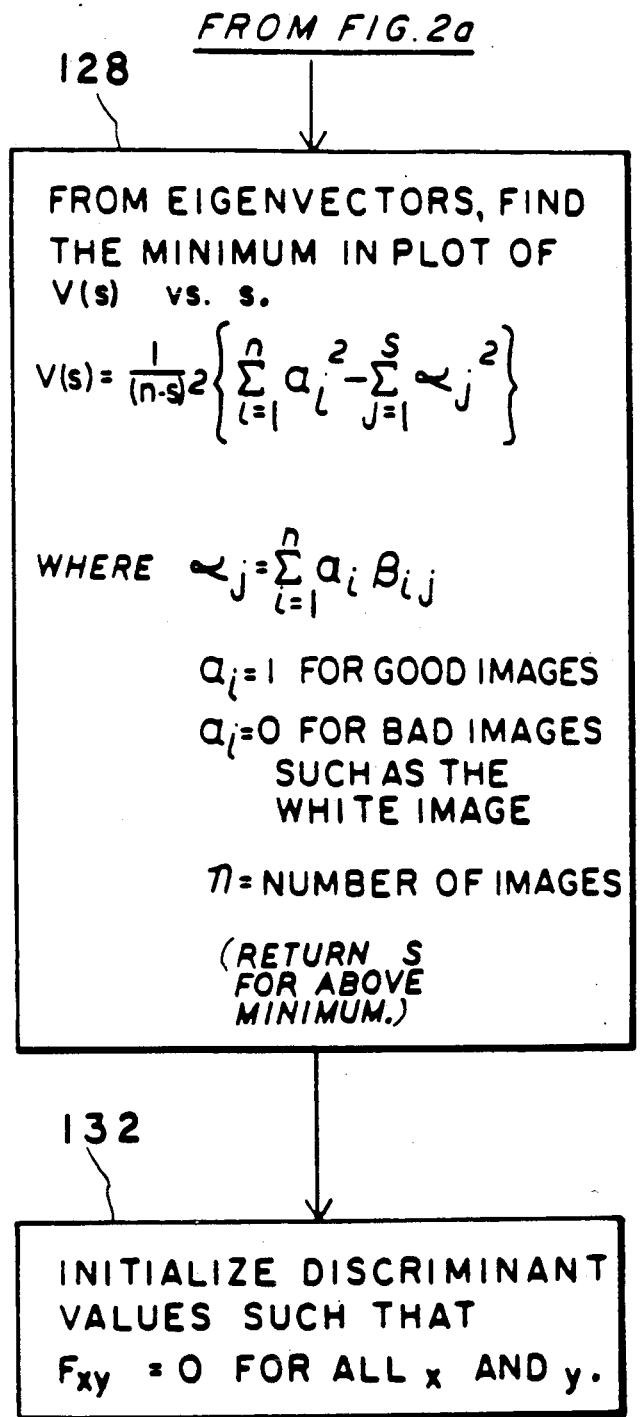
Figure 2B:
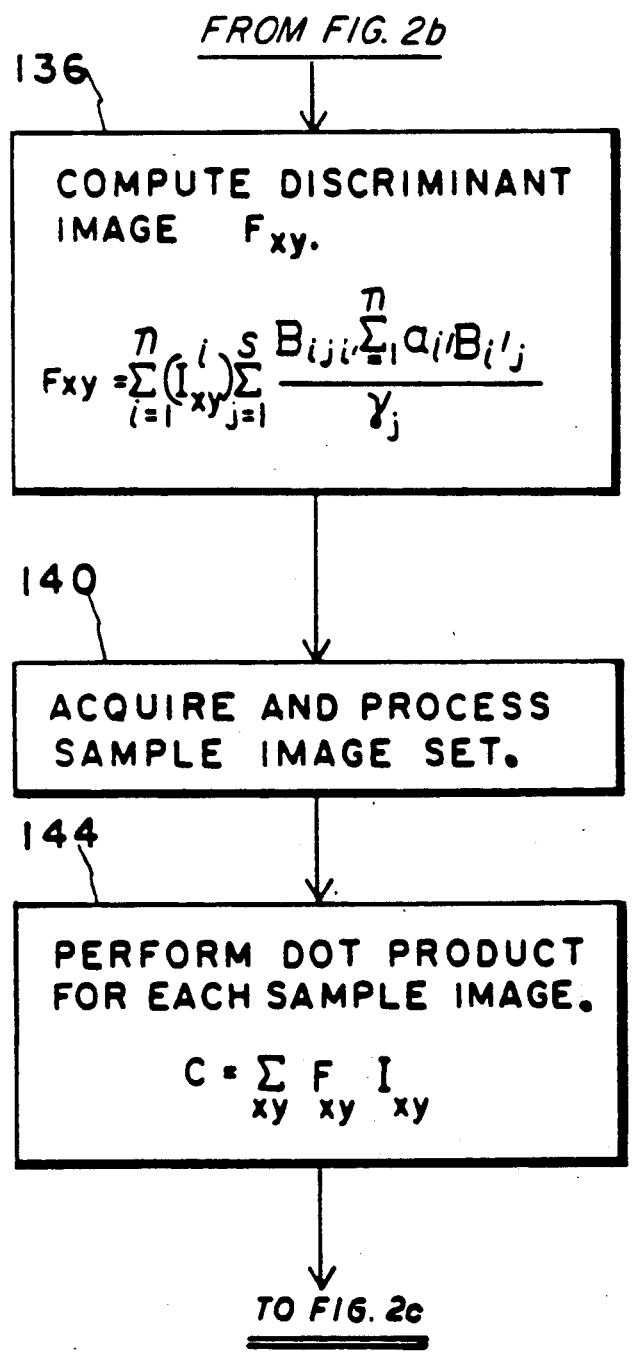

The method of this invention, which is largely carried out by elements 26 and 26A (preferably in accordance with the flow chart shown in FIG. 2), involves preprocessing a statistically significant number (e.g., 100 or 200) of images of products that are known to be acceptable (so-called "training products" or "training images") in order to enable processor 26 to construct a discriminant image for use in subsequent processing of products whose acceptability is unknown and therefore to be determined. Although the training images could be generated or acquired in any of a number of ways, the simplest method is generally to operate apparatus 10 with the desired number of training products 12. During processing of the training products, conveyor branch 20B is preferably locked in either one of its two positions. FIG. 2 will now be described.

Figure 3A:
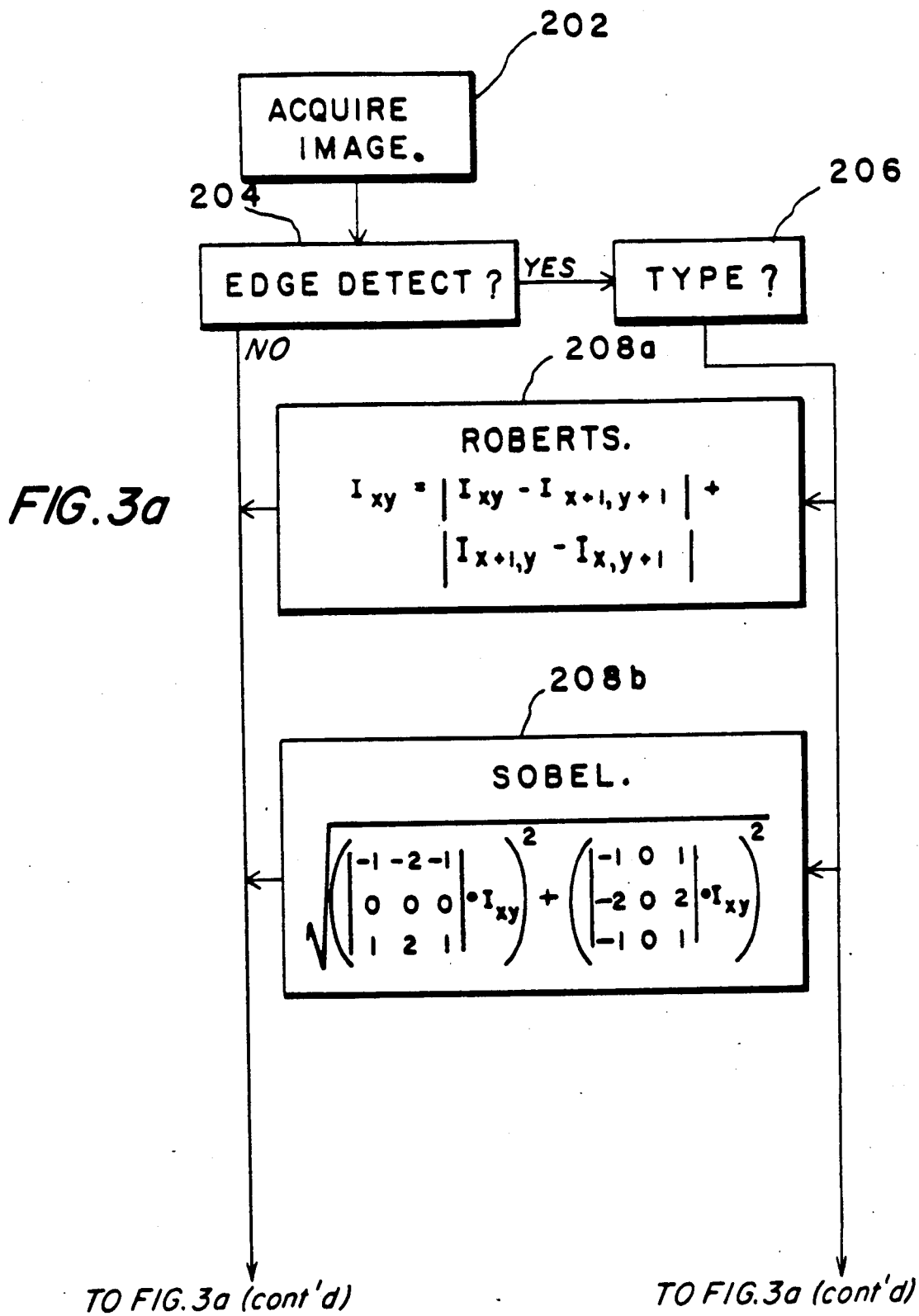
FIG. 3a and 3b (referred to collectively as FIG. 3) are a more detailed flow chart of portions of the flow chart of FIG. 2.

In step 102 processor 26 initializes various program constants and reads various program control inputs (e.g., from an associated keyboard (not shown)), as is conventionally done at the start of a computer program. In step 104 processor 26 uses camera 24 and imaging hardware 26A to acquire a set of training images exactly as described above in connection with FIG. 1. Imaging hardware 26A digitizes the typically analog output signal information of camera 24 to produce a digitized version of the training image. For example, imaging hardware 26A may break the image down into a grid of 256 by 256 pixels and assign a digital value (proportional to brightness) to each pixel. (Although a 256 by 256 grid has been mentioned for purposes of illustration, any other grid size, proportions, or number of subdivisions could be used if desired. For greater resolution, for example, the grid could be 512 by 512 pixels. In any event, note that the number of training images employed is typically less than the number of pixels.) The resulting image data is variously referred to herein as I, $I_{xy}$, or $\underline{I}$ (and this same notation is used even after possible modification of the image data in such subsequent steps as the edge detection, centering and aligning, and binarizing steps described below). Each training image is processed as shown in FIG. 3, which will now be described.

Figure 5:
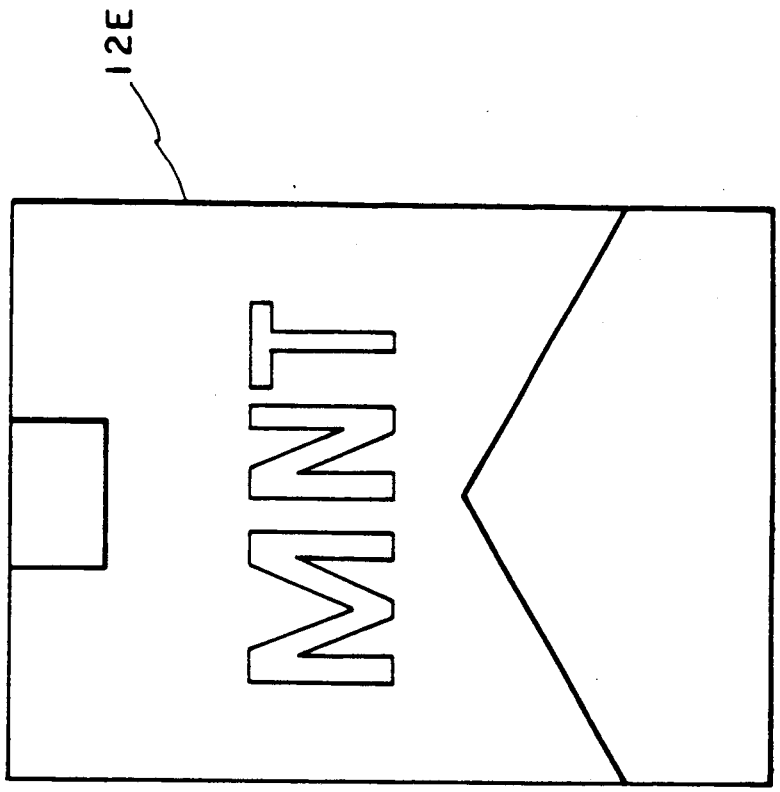
FIG. 5 is a view of the product image of FIG. 4 after partial processing in accordance with this invention.
Figure 4:
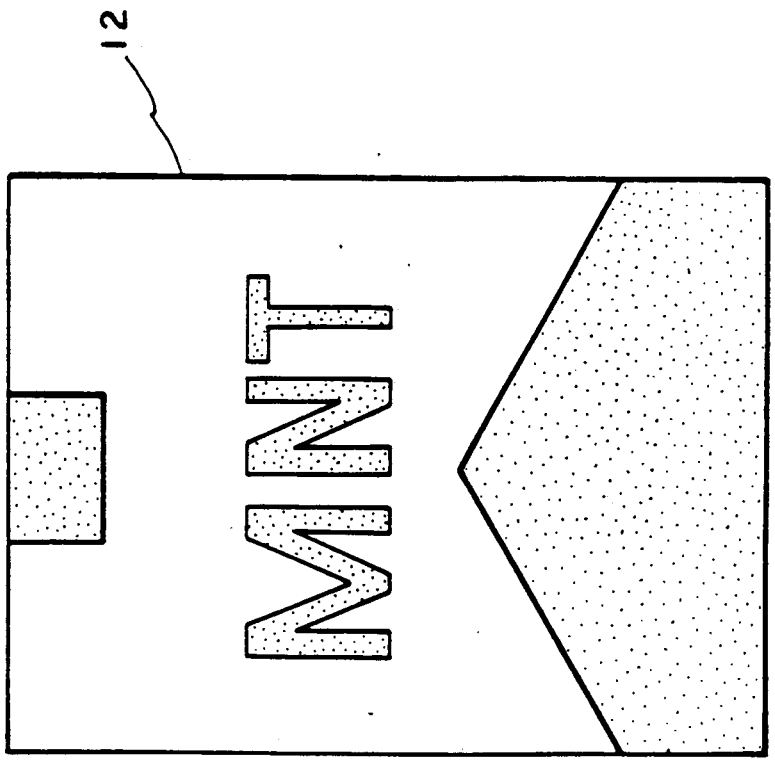
FIG. 4 is a view of a typical product image which can be processed in accordance with this invention.

Step 202 is merely a restatement of the portion of step 104 which relates to acquisition of an image. In step 204 one or more program control values (input in step 102) are tested to determine whether or not edge detection is to be performed. Edge detection is a well known technique which can be carried out in any of several different ways (see, for example, *Digital Image Processing* by Rafael C. Gonzalez, Addison-Wesley Publishing Company, 1987, pp. 331-41, and *Digital Image Processing* by William K. Pratt, John Wiley & Sons, Inc., 1978, pp. 478-92). In general, edge detection means that processor 26 alters the initial digital values of the pixels to produce output digital values such that pixels at or near significant changes in pixel value have output digital values which are relatively emphasized, while pixels which are not at or near significant changes in pixel value have output digital values which are relatively de-emphasized. For example, FIG. 4 shows a typical image prior to performance of edge detection, while FIG. 5 shows the same image after edge detection. (Although only the meaningful portion of the image is shown in FIGS. 4 and 5, it will be understood that the image frame is typically larger than the product image.) As FIGS. 4 and 5 illustrate, pixels associated with transitions from bright to dark (i.e., "edges") in the input image (FIG. 4) tend to come out bright in the edge detected image (FIG. 5). (For convenience herein the "bright" portions of FIG. 5 are represented by the linework in that FIG.)

If edge detection is to be performed (as it is in the preferred embodiments), then step 206 is performed to identify the edge detection technique to be employed, again based on testing one or more program control values input in step 102. Although other edge detection techniques are known and may be employed if desired, four such techniques (described in the above-mentioned textbook by Pratt and respectively referred to herein as the "Roberts," "Sobel," "Laplacian," and "lowpass" techniques) are provided in alternative steps 208a-d in FIG. 3. For example, if the Roberts technique (step 208a) is selected, each output digital value $I_{xy}$ is given by the equation in box 208a in FIG. 3 (where x and y are the associated pixel coordinates, and the values in the equal sign are the abovementioned input digital values (prior to edge detection)). Alternatively, if any of the Sobel, Laplacian, or lowpass edge detection techniques are selected in step 206, then the output digital values are computed using the relationship shown in the corresponding box 208 in FIG. 3.

After edge detection (if any) as described above, control passes to step 220 where the THRESHOLD constant (established in step 102) is tested to determine whether or not it is 0. If the THRESHOLD constant is not 0, binarization of the image data has been requested. If so, control passes to step 222 in which each image data value which is greater than the THRESHOLD value is set equal to 1, and all other image data values are set equal to 0 as shown by the relationships in box 222 in FIG. 3. Note that FIG. 5 is the result of both edge detection and binarization. Binarization is performed in the preferred embodiments because it greatly increases the speed with which the data can be further processed and because it reduces the sensitivity of the process to variations in light level.

After binarization (if any) as described above, control passes to step 230 in which the "first moments" of the image are computed (using the equations in box 230 in FIG. 3) in order to make it possible to subsequently center and align successive images with one another. In these equations K and L are pixel coordinate indexes (like x and y in the preceding equations). Accordingly, these equations compute the coordinates K' and L' of a reference point in each image which is substantially the same for all images. The data for each image can then be aligned with the data for all other images by shifting the data for each image (after the first image) so that the reference point for each image after the first image coincides with the reference point of the first image. (It may not be necessary to actually shift the image data to align the images. Rather, it may be sufficient to merely take into account the computed misalignment when further processing the data for each image.)

Figure 6:
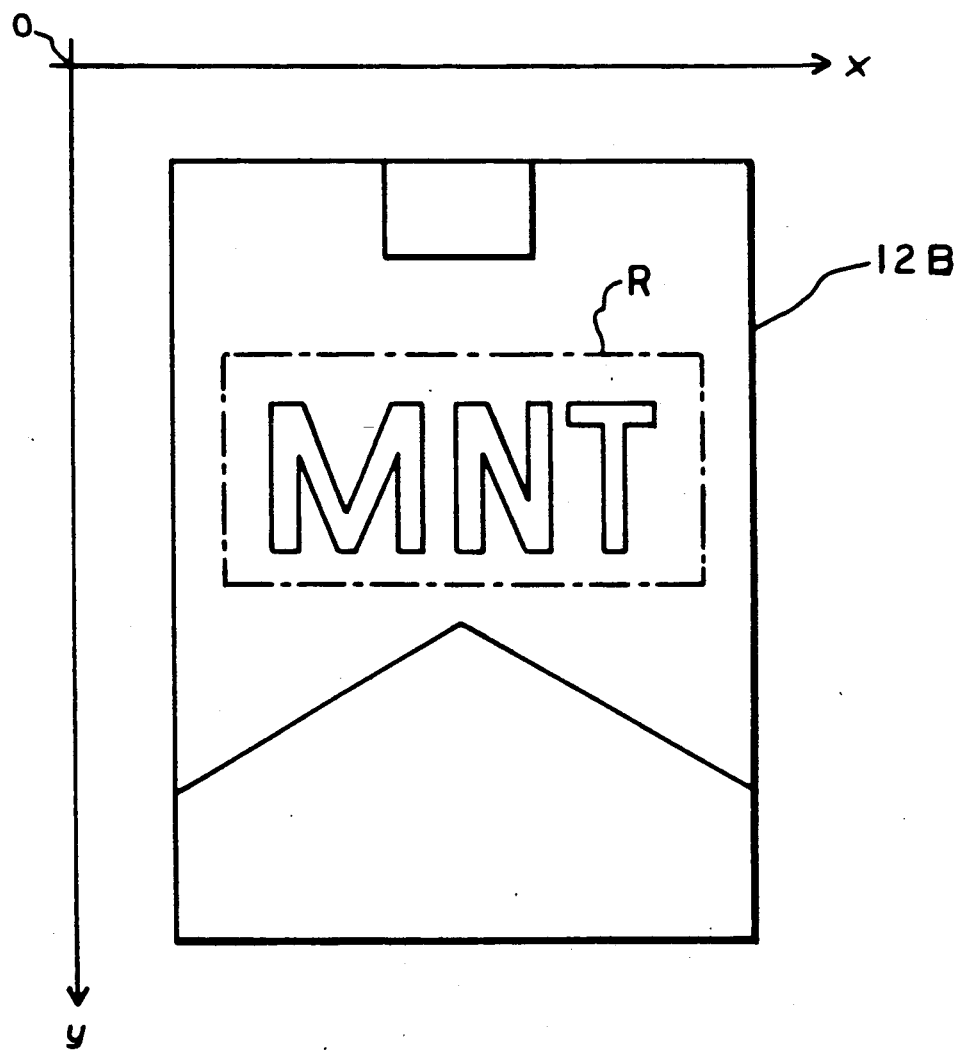
FIG. 6 is a view similar to FIG. 5 illustrating the manner in which the product image may be further processed in accordance with this invention.

Note that K and L need not span the entire image if there is some informative portion of the image which is relatively isolated from other significant portions of the image. For example, the region bounded by the chain-dotted line R in FIG. 6 might be selected as the domain of K and L if it were known that the binarized training image 12B could never move so much relative to that region that any of the letters "MNT" or any of the other image detail would cross the boundary of that region.

Figure 7:
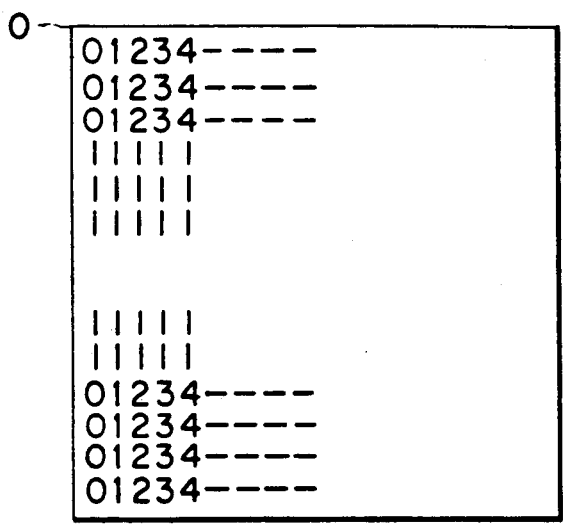
FIGS. 7, 8, 9, and 10 are simplified representations of frame data useful in explaining further image processing steps in accordance with this invention.
Figure 8:
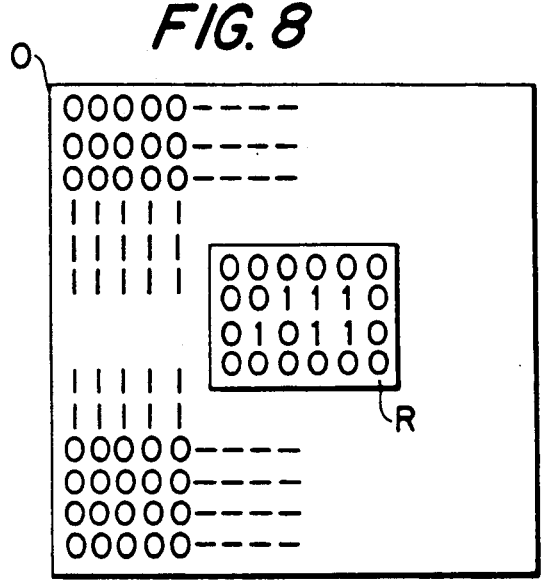

In step 230 the computation of variable a can be facilitated by having processor 26 form the logical AND of data like that depicted in FIGS. 7 and 8. FIG. 7 is a frame of data in which all rows are the same and in which each pixel position contains the value x of that pixel position. FIG. 8 is a frame of data in which all entries outside the region R are 0, while the actual binarized image data is preserved within the region R. (FIG. 8 includes greatly simplified, purely hypothetical image data.) The variable a results from forming the logical AND of the FIG. 7 and FIG. 8 data and then summing all of the resulting data.

Figure 9:
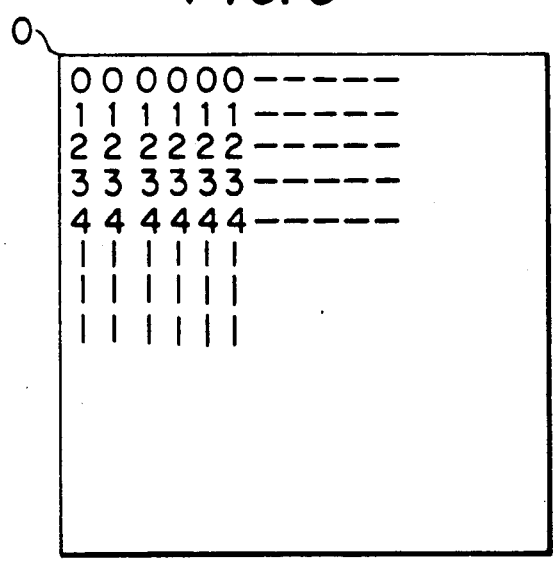

Computation of the variable b in step 230 can be facilitated by having processor 26 form the logical AND of the data depicted in FIG. 9 and the data depicted in FIG. 8. FIG. 9 is a frame of data in which all columns are the same and in which each pixel position contains the y coordinate of that pixel position. The variable b results from forming the logical AND of the FIG. 9 and FIG. 8 data and then summing all of the resulting data.

Figure 10:
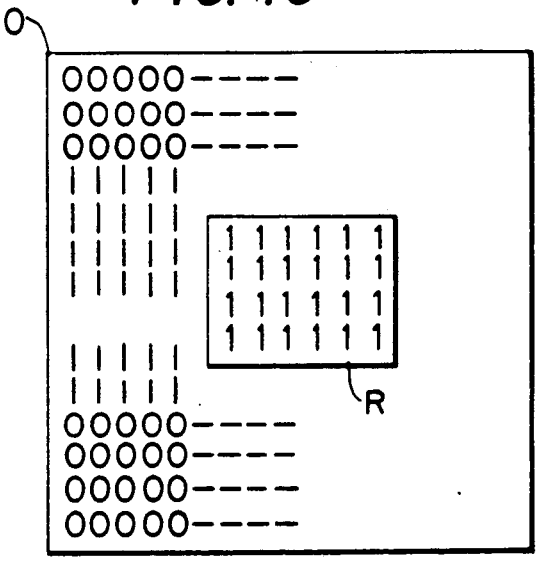

Computation of the variable c in step 230 can be facilitated by having processor 26 form the logical AND of the data depicted in FIG. 8 and FIG. 10. FIG. 10 is a frame of data which is 0 everywhere outside of region R and 1 everywhere inside of region R. The variable c results from forming the logical AND of the FIG. 10 and FIG. 8 data and then summing all of the resulting data.

Figure 3B:
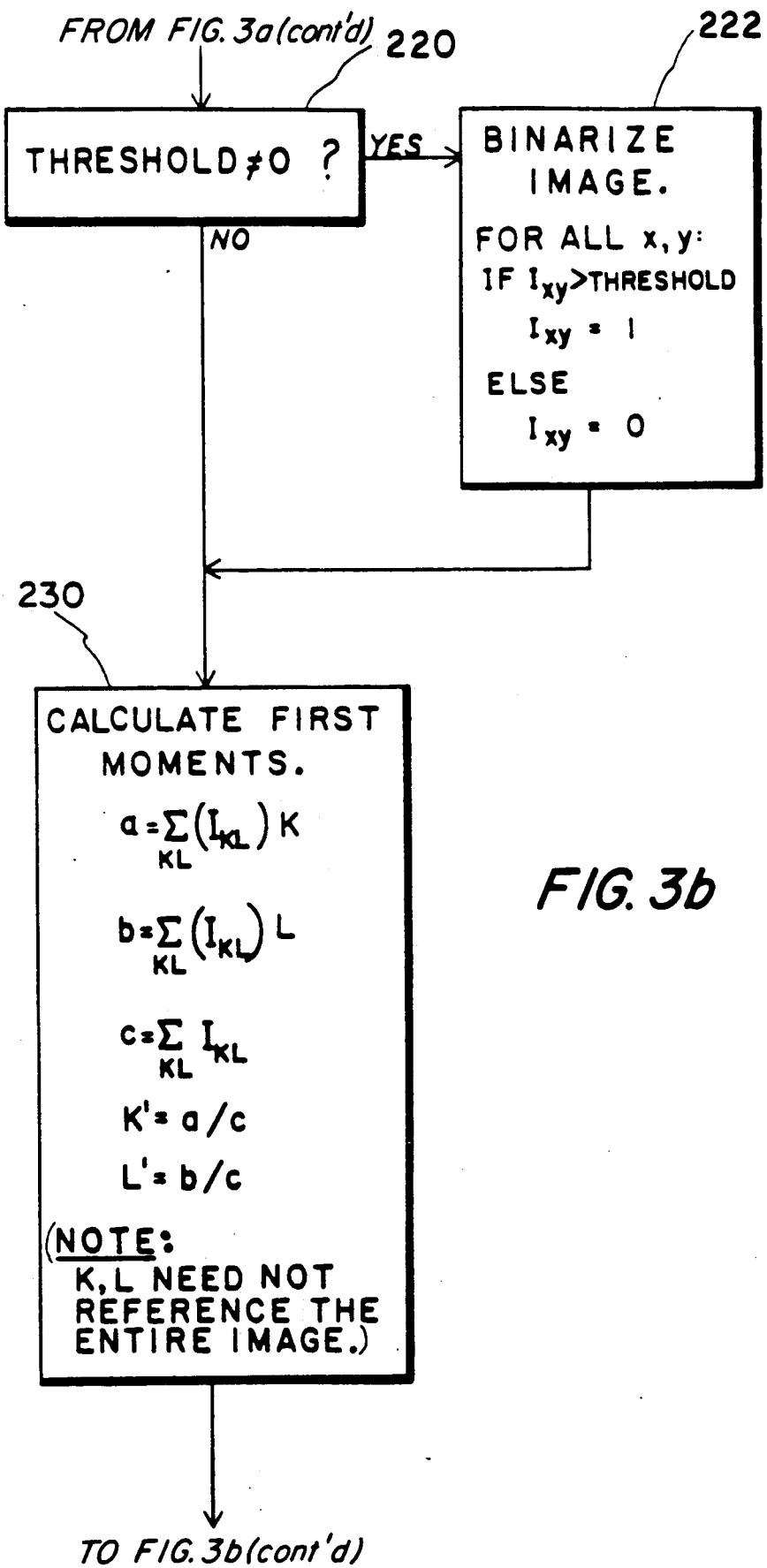
Figure 3B:
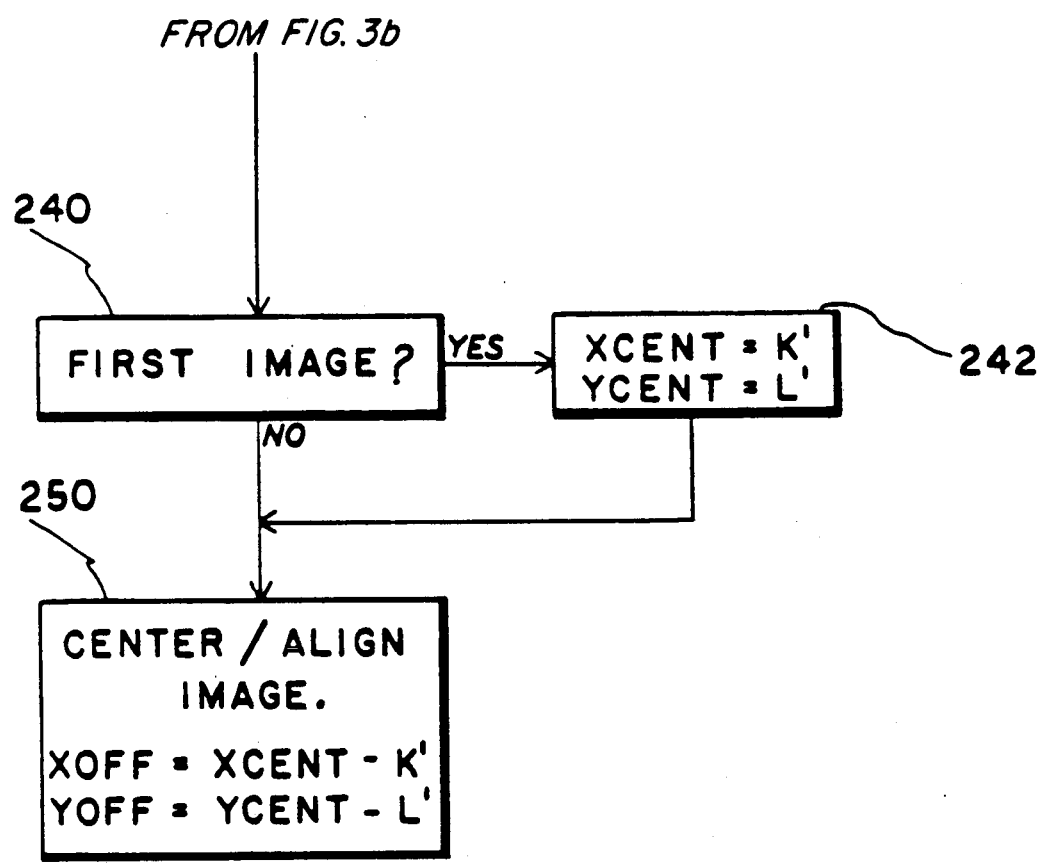

Continuing with FIG. 3b, after performing step 230, step 240 determines whether the image being processed is the first image. If so, step 242 is performed to set the variables XCENT and YCENT equal to the just-computed values of K' and L', respectively, and control then passes to step 250. Otherwise control passes directly to step 250.

In step 250 the image data is shifted (if necessary) to align each subsequent image with the first image. This is done by superimposing the reference point at coordinates K' and L' for each subsequent image on the location of that point for the first image. The amount by which each image must be shifted is therefore given by the variables XOFF and YOFF, computed using the equations in step 250 in FIG. 3. All of the data for the image is therefore shifted by the amounts XOFF and YOFF as part of step 250. (Again, it may not be necessary to actually shift the image data as long as the values XOFF and YOFF are taken into account when further processing that data.)

Returning now to FIG. 2, after the steps of FIG. 3 have been performed for all of the training images, control passes to step 110. In step 110, if requested via one or more inputs read in step 102, a "white image" (e.g., all ones) is added to the image list. Although this step is not indispensible, the efficacy of the discriminant image F (to be used in the actual inspection of products and computed as described in detail below) can be improved by adding such a known "bad" image to the training image set.

In step 120 the dot product of the data for every possible image pair (including the "white image," if any) is computed (as shown by the equation in box 120 in FIG. 2), and the resulting dot product values are used as the entries in dot product matrix A.

Figure 11:
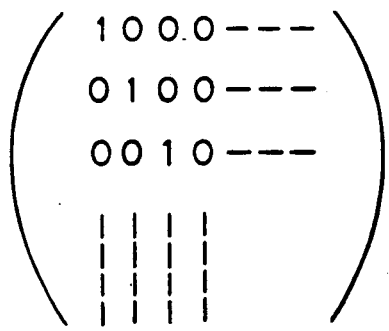
FIGS. 11 and 12 show matrices useful in explaining computations performed in accordance with this invention.
Figure 12:
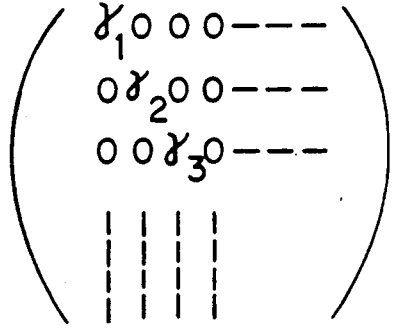

In step 124 eigenvalues $\gamma_j$ and eigenvectors $B_{ij}$ are calculated from the dot product matrix A. In particular, given $\underline{A}$ (a real, symmetric matrix), the matrices $\underline{A}$ and $\underline{G}$ are obtained by solving the equation $\underline{AB} = \underline{BG}$ such that $\underline{BB}^+ \underline{B}^+ \underline{B} = \underline{1}$, where $\underline{1}$ is matrix of the form shown in FIG. 11. Note that $(\underline{B}^+)_{ij} = B_{ji}$ and the eigenvalues $\gamma_i$ are the diagonal elements of $\underline{G}$, which is a matrix of the form shown in FIG. 12. Standard routines are available for solving these equations. See, for example, the IMSL, Inc. *Math Library* available from IMSL, Inc. of 2500 CityWest Boulevard, Houston, Tex. 77042-3020.

Step 128 is performed to determine the optimum amount of image information to be used in constructing the discriminant image F. This step is important because it reduces the sensitivity of the method to "noise" in the training images. If the discriminant image is calculated without performing this step, the effectiveness of the discriminant tends at first to improve as the number of training images increases, but to then degrade with further increases in the number of training images. Such degradation begins when redundancies in the training image set become significant (an effect which is difficult to predict). This problem is avoided by performing step 128.

Assuming a sufficient number of training images, the optimum discriminant image F generally results from using less than all of the available image information in the computation of the discriminant. Step 128 provides a simple procedure for reliably determining the point at which to truncate the image information used in the calculation of F.

Step 128 involves the computation of V as a function of s (an integer index variable which ranges from 1 to n, where n is the number of images in the training set). The equation for V is given in box 128 in FIG. 2. The value of s which gives the minimum value of V is determined as a result of the performance of step 128 and is used as described below in the performance of the subsequent steps.

In step 132 the discriminant image F (which is a two-dimensional matrix commensurate in size with the matrix of data for any actual image I) is initialized to 0. Then in step 136 the actual discriminant image values are computed using the equation in box 136 in FIG. 2. Note that the index j in this equation is truncated using the value of s returned after the performance of step 128. The discriminant image F computed in step 136 is therefore the optimum such image as explained above.

After the performance of step 136, processor 26 begins the performance of steps for determining an acceptance threshold or range to be used in conjunction with the discriminant image in the actual optical inspection process. In step 140 a statistically significant number (e.g., 50) of further training images (sometimes referred to herein as sample images to distinguish them from the training images processed in step 104) is acquired and processed as shown in FIG. 3. It is desirable for the sample images to be good images representative of the range of product images that will be encountered during the actual product inspection process. It is also desirable to know the standard deviation among good images so that a threshold value can be selected (in step 148 discussed below) that will result in false rejection of less than a given fraction of acceptable units.

In step 144 processor 26 computes the dot product of the discriminant image F and each sample image I using the equation in box 144 in FIG. 2. If the sample image is an acceptable image, the resulting value of C will be 1 or close to 1 (the value of $a_i$ used for good images in step 128). The more unacceptable the image, the farther C will be from 1.

After step 144 has been performed for each sample image, processor 26 performs step 148 in which the values of C for all of the sample images are processed using conventional techniques to compute their average ($C_{av}$) and the standard deviation $\sigma$ of their distribution. Thereafter, processor 26 computes threshold values $C_{th}$ equal to $C_{av}$ plus or minus a predetermined number of multiples of $\sigma$. For example, if the objective of the optical inspection process is to erroneously reject no more than about one acceptable product in 1000, then the values of $C_{th}$ are given by the equation in box 148 in FIG. 2 (a Gaussian distribution being assumed).

The apparatus of the invention is now ready to perform actual product inspections in accordance with the further steps shown in FIG. 2. In step 152 the image of a product to be inspected is acquired and processed as shown in detail in FIG. 3 and described above. In step 156 processor 26 computes the dot product D of the discriminant image F and the product image data I using the equation shown in box 156 in FIG. 2. As in the case of step 144, D will be 1 or close to 1 if the product has an acceptable image. D will be farther from 1 the more unacceptable the product image is.

In step 160 processor 26 compares D to the acceptance range determined in step 148. If D is between the upper and lower limits of the acceptance range, processor 26 performs step 164a to accept the product (i.e., by controlling conveyor branch 20B to convey the product to conveyor segment 20A). On the other hand, if D is outside the range bounded by the upper and lower limits of the acceptance range, processor 26 performs step 164b to reject the product (i.e., by controlling conveyor branch 20B to convey the product to conveyor segment 20R). Steps 152-164 are performed for each product 12 to be inspected.

The following additional information may be helpful in understanding the principles underlying the invention as described above. In general, the object is to compute a discriminant image F such that the following relationships are satisfied:

$$\sum_{xy} F_{xy} I_{xy} \cong 1 \quad \text{for all ``good'' training images} \quad (1)$$

$$\sum_{xy} F_{xy}^2 \cong \text{minimum} \quad (2)$$

The number 1 in Equation (1) is merely an arbitrary, preferably nonzero, constant associated with a "good" or "acceptable" image.

If desired, the efficacy of the discriminant image can be improved by additionally requiring the following relationship to be satisfied:

$$\sum_{xy} F_{xy} \cong 0 \quad (3)$$

This requirement corresponds to the inclusion of the above-mentioned "white image" in the data set. The number 0 in Equation (3) is a constant associated with a "bad" or "unacceptable" image.

The efficacy of the discriminant image can be still further improved, if desired, by processing one or more images that are known to be unacceptable and making the discriminant image additionally satisfy the following relationship for each unacceptable image $I^u$:

$$\sum_{xy} F_{xy} I^u_{xy} \cong 0 \quad (4)$$

The solution of Equations (1) and (2) (together with Equation (3) and/or (4) if desired) is simplified by constructing the discriminant image from a set of orthogonal images or "eigenimages" $\Phi^{(j)}$, where $$\underline{\Phi^{(j)}} = \sum_{i=1}^{n} \underline{I^{(i)}} B_{ij} \quad (5)$$

In Equation (5) n is the total number of training images (including any "white image" and any unacceptable images $I^u$), i is a training image index, and j is an eigenimage index. Indexes i and j both run from 1 to n.

The transformation matrix B in Equation (5) is orthogonal. That is $$\underline{B} \cdot \underline{B}^+ = \underline{B}^+ \cdot \underline{B} = 1 \quad (6)$$

and $$\underline{\Phi^i} \cdot \underline{\Phi^j} = G_{ij} = \gamma_i \delta_{ij} \quad (7)$$

It follows that:

$$\underline{AB} = \underline{BG} \quad (8)$$

where $A_{ij} = \underline{I^{(i)}} \cdot \underline{I^{(j)}}$ as in step 120 of FIG. 2. Thus the columns of the transformation matrix B simply the eigenvectors of the matrix A.

The discriminant image $\underline{F}$ is formed from a truncated linear combination of the eigenimages defined above as follows:

$$\underline{F} = \sum_{j=1}^{s} C_j \underline{\Phi^{(j)}} \quad (9)$$

where it is assumed that the eigenimages are ordered such that $\gamma_1 > \gamma_2 > \ldots > \gamma_n$. (C in these equations is unrelated to C in steps 144, 148, and 160.) The series is truncated at $s < n$ functions in order to avoid the incorporation of noise in the discriminant image.

A unique feature of the approach presented here is the method for choosing s. The method of generalized cross-validation is used (see G. H. Golub et al., "Generalized Cross-Validation as a Method for Choosing a Good Ridge Parameter," *Technometrics*, Vol. 21, No. 2, 1979), but the orthogonal transformation introduced above greatly simplifies the implementation of this method. The truncation level s is chosen to be the value for which $$V(s) = \frac{1}{(n-s)^2} \left\{ \sum_{i=1}^{n} a_i^2 - \sum_{j=1}^{s} \left[ \sum_{i=1}^{n} a_i B_{ij} \right]^2 \right\} \quad (10)$$

is a minimum. This is the determination made in step 128 in FIG. 2, and as in step 128 $a_i$ here is 1 for good images and 0 for the "white" or any other bad image. Having chosen s, the coefficients $C_j$ for Equation (9) are chosen so that $$W = \sum_i [\underline{F} \cdot \underline{I}^{(i)} - a_i]^2 \qquad (11)$$

is a minimum. It follows that $$C_j = \frac{1}{\gamma_j} \sum_{i=1}^{n} a_i B_{ij} \qquad (12)$$

Therefore, $$\underline{F} = \sum_{j=1}^{s} \frac{1}{\gamma_j} \left[ \sum_{i=1}^{n} a_i B_{ij} \right] \underline{\Phi}^{(j)} \qquad (13)$$

which corresponds to the computation performed in step 136 in FIG. 2

The foregoing method for determining the discriminant image $\underline{F}$ is unique in that the discriminant function is expressed as a linear combination of eigenimages with the series truncated at s terms. The effect of this truncation is to reduce the sensitivity of the method to noise in the training images. As has been mentioned, if the discriminant image is calculated without this truncation, the effectiveness of the discriminant at first improves as the number of training images increases, but then begins to degrade with the addition of further training images. Such degradation begins when redundancies in the training set become significant (an effect which is hard to predict). This problem is avoided in the method set forth above by truncating the eigenimage series at s images. Moreover, the present method includes a simple procedure for reliably determining the optimum value for s.

It will be noted that the systems of this invention effectively train themselves to deal with each new product inspection task. Each time a different product is to be inspected, the training portion of the invention (steps 102–148) is performed to allow the system to acquire the information needed to establish appropriate inspection criteria. The systems of this invention are therefore of universal application and do not require extensive set-up by a highly skilled operator. Note also that the systems of this invention advantageously inspect the entire image of a product, not just predetermined portions of such images.

It will be understood that the foregoing is merely illustrative of the principles of the invention, and that various modifications can be made by those skilled in the art without departing from the scope and spirit of the invention. For example, although image frames of 256 by 256 pixels have been mentioned, other image frame sizes and shapes can be used if desired.

We claim:

1. The method of determining whether or not a surface of an object has substantially the same appearance as the corresponding surface of a plurality of training objects, said method comprising the steps of:

for each training object, (a) forming a two-dimensional image of said surface, (b) subdividing said two-dimensional image into a plurality of pixels, (c) digitizing each of said pixels by associating with each pixel an initial digital value proportional to an optical characteristic of the associated pixel, (d) edge detecting said initial digital values by processing said initial digital values to produce output digital values such that initial digital values associated with pixels at or near substantial changes in initial digital value are relatively emphasized to produce the associated output digital values, while initial digital values associated with all other pixels are relatively de-emphasized to produce the associated output digital values, and (e) binarizing each of said output digital values by associating a first binary value with each of said output digital values which is on one side of a first predetermined threshold value and by associating a second binary value with each of said output digital values which is on the other side of said first predetermined threshold value;

associating a discriminant value with each of said pixels, each discriminant value being chosen so that, for each training object, the dot product of the discriminant values and the binary values is approximately a predetermined nonzero constant value;

repeating steps (a)–(e) for said object; and comparing the dot product of said discriminant values and the binary values for said object to said predetermined nonzero constant value.

2. The method defined in claim 1 wherein said discriminant values collectively comprise a discriminant image $\underline{F}$ and wherein said method further comprises the steps of:

converting the binary values associated with said training objects to a plurality of eigenimages $\Phi^{(j)}$, all of said eigenimages being orthogonal to one another; and forming said discriminant image from a truncated linear combination of said eigenimages.

3. The method defined in claim 2 wherein the binary values associated with each of said training objects i collectively comprise a training image $\underline{I}^{(i)}$, and wherein said method further comprises the step of:

computing each of said eigenimages as in the equation:

$$\underline{\phi}^{(j)} = \sum_{i=1}^{n} \underline{I}^{(i)} B_{ij}$$

where n is the total number of training images and the transformation matrix B is orthogonal.

4. The method defined in claim 3 wherein said step of forming said discriminant image from a truncated linear combination of said eigenimages comprises the step of:

computing said discriminant image as in the equation:

$$\underline{F} = \sum_{j=1}^{s} C_j \underline{\phi}^{(j)}$$

where s is an integer less than n.

5. The method defined in claim 4 further comprising the step of:

selecting the value of s for the equation in claim 4 which gives the minimum value for V(s), where V(s) is computed as in the equation:

$$V(s) = \frac{1}{(n-s)^2} \left( \sum_{i=1}^{n} a_i^2 - \sum_{j=1}^{s} \left[ \sum_{i=1}^{n} a_i B_{ij} \right]^2 \right)$$

where $a_i$ is a nonzero constant for all good training images and zero for any bad training images.

6. The method defined in claim 5 further comprising the step of:

computing the values $C_j$ for the equation of claim 4 as in the equation:

$$C_j = \frac{1}{\gamma_j} \sum_{i=1}^{n} a_i B_{ij}$$

where the eigenvalues $\gamma_j$ are the diagonal elements of a matrix $\underline{\underline{G}}$ given by the equation $\underline{\underline{AB}} = \underline{\underline{BG}}$, where $\underline{\underline{A}}$ is the real, symmetric matrix given by the dot product of every possible training image pair, and the transformation matrix B is such that $\underline{\underline{BB^+}} = \underline{\underline{B^+B}} = \underline{\underline{1}}$.

7. The method defined in claim 6 wherein said eigenimages are ordered such that $\gamma_1 > \gamma_2 > \gamma_3 > \ldots > \gamma_n$.

8. The method defined in claim 1 wherein said discriminant values are additionally chosen so that the sum of the squares of the discriminant values is approximately minimized.

9. The method defined in claim 1 wherein said discriminant values are additionally chosen so that the sum of the discriminant values is approximately zero.

10. The method defined in claim 1 wherein said two-dimensional images of said training objects may not be in registration with one another, and wherein, prior to said step of associating a discriminant value with each of said pixels, said method further comprises the steps of:

for each training object, (f) computing the center of gravity of at least a portion of the associated two-dimensional image, and (g) shifting the associated binary values so that the centers of gravity associated with all of said training objects are approximately coincident.

11. The method defined in claim 10 wherein, after repeating steps (a)-(e) for said object, said method further comprises the steps of:

computing the center of gravity of at least a portion of the two-dimensional image associated with said object; and shifting the binary values associated with said object so that the center of gravity associated with said object is approximately coincident with the approximately coincident centers of gravity associated with said training objects.

12. The method defined in claim 1 wherein a plurality of sample objects representative of the range of variation likely to occur among acceptable objects is available, and wherein, prior to said step of repeating steps (a)-(e) for said object, said method further comprises the steps of:

repeating steps (a)-(e) for each sample object;

computing a correlation value for each sample object by forming the dot product of said discriminant values and the binary values for said sample object;

computing the average of the correlation values for all of said sample objects;

computing the standard deviation of the correlation values for all of said sample objects; and computing first and second threshold correlation values respectively equal to said average of the correlation values plus or minus predetermined numbers of said standard deviation.

13. The method defined in claim 12 wherein said step of comparing the dot product of said discriminant values and the binary values for said object to said predetermined nonzero constant value comprises the step of:

determining whether or not said dot product of said discriminant values and the binary values for said object is between said first and second threshold correlation values.

14. The method defined in claim 1 wherein at least one unacceptable object is available, and wherein said step of associating a discriminant value with each of said pixels comprises the steps of:

repeating steps (a)-(e) for said unacceptable object; and additionally choosing said discriminant values so that the dot product of the discriminant values and the binary values associated with said unacceptable object is approximately zero.

15. The method defined in claim 1 wherein the number of pixels is substantially greater than the number of training objects.

16. Apparatus for determining whether or not a surface of an object has substantially the same appearance as the corresponding surface of a plurality of training objects comprising:

means for, for each training object, (a) forming a two-dimensional image of said surface, (b) subdividing said two-dimensional image into a plurality of pixels, (c) digitizing each of said pixels by associating with each pixel an initial digital value proportional to an optical characteristic of the associated pixel, (d) edge detecting said initial digital values by processing said initial digital values to produce output digital values such that initial digital values associated with pixels at or near substantial changes in initial digital value are relatively emphasized to produce the associated output digital values, while initial digital values associated with all other pixels are relatively de-emphasized to produce the associated output digital values, and (e) binarizing each of said output digital values by associating a first binary value with each of said output digital values which is on one side of a first predetermined threshold value and by associating a second binary value with each of said output digital values which is on the other side of said first predetermined threshold value;

means for associating a discriminant value with each of said pixels, each discriminant value being chosen so that, for each training object, the dot product of the discriminant values and the binary values is approximately a predetermined non-zero constant value;

means for repeating functions (a)-(e) with respect to said object; and means for comparing the dot product of said discriminant values and the binary values for said object to said predetermined nonzero constant value.

17. The apparatus defined in claim 16 wherein said discriminant values collectively comprise a discriminant image $\underline{F}$ and wherein said apparatus further comprises:

means for converting the binary values associated with said training objects to a plurality of eigenimages $\underline{\Phi}^{(j)}$, all of said eigenimages being orthogonal to one another; and means for forming said discriminant image from a truncated linear combination of said eigenimages.

18. The apparatus defined in claim 17 wherein the binary values associated with each of said training objects i collectively comprise a training image $\underline{I}^{(i)}$, and wherein said apparatus further comprises:

means for computing each of said eigenimages as in the equation:

$$\underline{\phi}^{(j)} = \sum_{i=1}^{n} I^{(i)} B_{ij}$$

where n is the total number of training images and the transformation matrix B is orthogonal.

19. The apparatus defined in claim 18 wherein said means for forming said discriminant image from a truncated linear combination of said eigenimages comprises:
means for computing said discriminant image as in the equation:

$$\underline{F} = \sum_{j=1}^{s} C_j \underline{\phi}^{(j)}$$

where s is an integer less than n.

20. The apparatus defined in claim 19 further comprising:
selecting the value of s for the equation of claim 19 which gives the minimum value for V(s), where V(s) is computed as in the equation:

$$V(s) = \frac{1}{(n-s)^2} \left( \sum_{i=1}^{n} a_i^2 - \sum_{j=1}^{s} \left[ \sum_{i=1}^{n} a_i B_{ij} \right]^2 \right)$$

where $a_i$ is a nonzero constant for all good training images and zero for any bad training images.

21. The apparatus defined in claim 20 further comprising:
means for computing the values $C_j$ for the equation of claim 19 as in the equation:

$$C_j = \frac{1}{\gamma_j} \sum_{i=1}^{n} a_i B_{ij}$$

where the eigenvalues $\gamma_j$ are diagonal elements of a matrix $\underline{G}$ given by the equation $\underline{AB} = \underline{BG}$, where $\underline{A}$ is the real, symmetric matrix given by the dot product of every possible training image pair, and the transformation matrix $\underline{B}$ is such that $\underline{BB}^+ = \underline{B}^+\underline{B} = \underline{1}$.

22. The apparatus defined in claim 21 wherein said eigenimages are ordered such that $\gamma_1 > \gamma_2 > \gamma_3 > \cdots > \gamma_n$.

23. The apparatus defined in claim 16 wherein said discriminant values are additionally chosen so that the sum of the squares of the discriminant values is approximately minimized.

24. The apparatus defined in claim 16 wherein said discriminant values are additionally chosen so that the sum of the discriminant values is approximately zero.

25. The apparatus defined in claim 16 wherein said two-dimensional images of said training objects may not be in registration with one another, and wherein, prior to operation of said means for associating a discriminant value with each of said pixels, said apparatus further comprises:
means for, for each training object, (f) computing the center of gravity of at least a portion of the associated two-dimensional image, and (g) shifting the associated binary values so that the centers of gravity associated with all of said training objects are approximately coincident.

26. The apparatus defined in claim 25 wherein said means for repeating functions (a)-(e) with respect to said object comprises:
means for computing the center of gravity of at least a portion of the two-dimensional image associated with said object; and
means for shifting the binary values associated with said object so that the center of gravity associated with said object is approximately coincident with the approximately coincident centers of gravity associated with said training objects.

27. The apparatus defined in claim 16 wherein a plurality of sample objects representative of the range of variation likely to occur among acceptable objects is available, and wherein, prior to operation of said means for repeating functions (a)-(e) with respect to said object, said apparatus further comprises the steps of:
means for repeating functions (a)-(e) with respect to each sample object;
means for computing a correlation value for each sample object by forming the dot product of said discriminant values and the binary values for said sample object;
means for computing the average of the correlation values for all of said sample objects;
means for computing the standard deviation of the correlation values for all of said sample objects; and
means for computing first and second threshold correlation values respectively equal to said average of the correlation values plus or minus predetermined numbers of said standard deviation.

28. The apparatus defined in claim 27 wherein said means for comparing the dot product of said discriminant values and the binary values for said object to said predetermined nonzero constant value comprises:
means for determining whether or not said dot product of said discriminant values and the binary values for said object is between said first and second threshold correlation values.

29. The apparatus defined in claim 16 wherein at least one unacceptable object is available, and wherein said means for associating a discriminant value with each of said pixels comprises:
means for repeating functions (a)-(e) with respect to said unacceptable object; and
means for additionally choosing said discriminant values so that the dot product of the discriminant values and the binary values associated with said unacceptable object is approximately zero.

30. The apparatus defined in claim 16 wherein the number of pixels is substantially greater than the number of training objects.

31. The method of determining whether or not an image to be inspected has substantially the same appearance as a plurality of training images, said method comprising the steps of:
digitizing each training image i to produce corresponding training image data $I^{(i)}$;
converting said training image data to a plurality of orthogonal eigenimages given by the equation:

$$\underline{\phi}^{(j)} = \sum_{i=1}^{n} I^{(i)} B_{ij}$$

where n is the total number of training images and the transformation matrix B is orthogonal;

computing a discriminant image F from a truncated linear combination of said eigenimages given by the equation:

$$\underline{F} = \sum_{j=1}^{s} C_j \underline{\phi}^{(j)}$$

where s is an integer less than n selected as a value which gives the minimum value for V(s) in the equation:

$$V(s) = \frac{1}{(n-s)^2} \left\{ \sum_{i=1}^{n} a_i^2 - \sum_{j=1}^{s} \left[ \sum_{i=1}^{n} a_i B_{ij} \right]^2 \right\}$$

where $a_i$ is a nonzero constant for all good training images and zero for any bad training images, and where the values $C_j$ are given by the equation:

$$C_j = \frac{1}{\gamma_j} \sum_{i=1}^{n} a_i B_{ij}$$

where the eigenvalues $\gamma_j$ are the diagonal elements of a matrix $\underline{\underline{G}}$ given by the equation $\underline{\underline{AB}} = \underline{\underline{BG}}$, where $\underline{\underline{A}}$ is the real, symmetric matrix given by the dot product of every possible training image pair, and the transformation matrix B, is such that $\underline{\underline{BB}}^+ = \underline{\underline{B}}^+\underline{\underline{B}} = \underline{\underline{1}}$;

digitizing said image to be inspected;

forming the dot product of said discriminant image and said digitized image to be inspected; and comparing said dot product to a predetermined reference value.

32. The method defined in claim 31 wherein said step of computing said discriminant image further comprises the step of:

selecting the individual values which make up said discriminant image so that the sum of the squares of all of said individual values is approximately minimized.

33. The method defined in claim 31 wherein said step of computing said discriminant image further comprises the step of:

selecting the individual values which make up said discriminant image so that the sum of all of said individual values is approximately zero.

34. The method defined in claim 31 wherein said eigenimages are ordered such that $\gamma_1 > \gamma_2 \gamma_3 > \ldots > \gamma_n$.

* * * * *